(12) United States Patent
Sweeney et al.

(10) Patent No.: US 11,839,740 B2
(45) Date of Patent: *Dec. 12, 2023

(54) INTRAOSSEOUS NEEDLE ASSEMBLY AND METHOD OF USE THEREOF

(71) Applicant: Spinal Generations, LLC, Mokena, IL (US)

(72) Inventors: Patrick J. Sweeney, Flossmoor, IL (US); Matthew V. Leyden, St. Paul, MN (US)

(73) Assignee: Spinal Generations, LLC, Mokena, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/977,111

(22) Filed: Oct. 31, 2022

(65) Prior Publication Data

US 2023/0052651 A1    Feb. 16, 2023

Related U.S. Application Data

(63) Continuation of application No. 15/844,246, filed on Dec. 15, 2017, now Pat. No. 11,517,666.

(51) Int. Cl.
*A61M 5/158* (2006.01)
*A61B 17/34* (2006.01)
(Continued)

(52) U.S. Cl.
CPC ......... *A61M 5/158* (2013.01); *A61B 17/3472* (2013.01); *A61B 2017/349* (2013.01);
(Continued)

(58) Field of Classification Search
CPC . A61B 17/34; A61B 17/3417; A61B 17/3421; A61B 17/3472; A61B 2017/349; A61M 2005/1586; A61M 2005/311; A61M 2005/3201; A61M 2005/3289; A61M 2210/02; A61M 5/158; A61M 5/32;
(Continued)

(56) References Cited

U.S. PATENT DOCUMENTS

| 4,670,008 A | * | 6/1987 | Von Albertini ... A61M 25/0606 |
| | | | 604/165.01 |
| 5,484,442 A | | 1/1996 | Melker et al. |

(Continued)

FOREIGN PATENT DOCUMENTS

DE      22 05 314      8/1973

OTHER PUBLICATIONS

International Search Report and Written Opinion on Appl. No. PCT PCT/U82018/065501, dated Apr. 4, 2019, 18 pages.

*Primary Examiner* — Shefali D Patel
(74) *Attorney, Agent, or Firm* — Foley & Larnder LLP

(57) ABSTRACT

An intraosseous needle includes a cylindrical shaft. The cylindrical shaft includes a first portion comprising a plurality of threads protruding from the cylindrical shaft. The cylindrical shaft includes a second portion comprising a plurality of fenestrations, disposed between the first portion and a distal end of the cylindrical shaft, wherein the cylindrical shaft is continuous and smooth within the second portion, and where the continuous, smooth second portion is longer than the first portion. The intraosseous needle also includes a needle head extending from a proximal end of the cylindrical shaft.

20 Claims, 9 Drawing Sheets

(51) Int. Cl.
　　　*A61M 5/32*　　　(2006.01)
　　　*A61M 5/42*　　　(2006.01)
　　　*A61M 5/46*　　　(2006.01)
　　　*A61M 5/31*　　　(2006.01)

(52) U.S. Cl.
　　　CPC ........... *A61M 5/329* (2013.01); *A61M 5/3291* (2013.01); *A61M 5/427* (2013.01); *A61M 5/46* (2013.01); *A61M 2005/311* (2013.01); *A61M 2210/02* (2013.01)

(58) Field of Classification Search
　　　CPC .. A61M 5/3286; A61M 5/3287; A61M 5/329; A61M 5/3291; A61M 5/3293; A61M 5/427; A61M 5/46
　　　See application file for complete search history.

(56) References Cited

U.S. PATENT DOCUMENTS

| | | | |
|---|---|---|---|
| 5,743,912 A * | 4/1998 | Lahille | A61B 17/742 606/65 |
| 6,210,376 B1 | 4/2001 | Grayson | |
| 6,221,029 B1 | 4/2001 | Mathis et al. | |
| 7,250,055 B1 * | 7/2007 | Vanderwalle | A61B 17/864 606/92 |
| 2009/0204024 A1 | 8/2009 | Miller | |
| 2011/0076640 A1 | 3/2011 | Jones | |

* cited by examiner

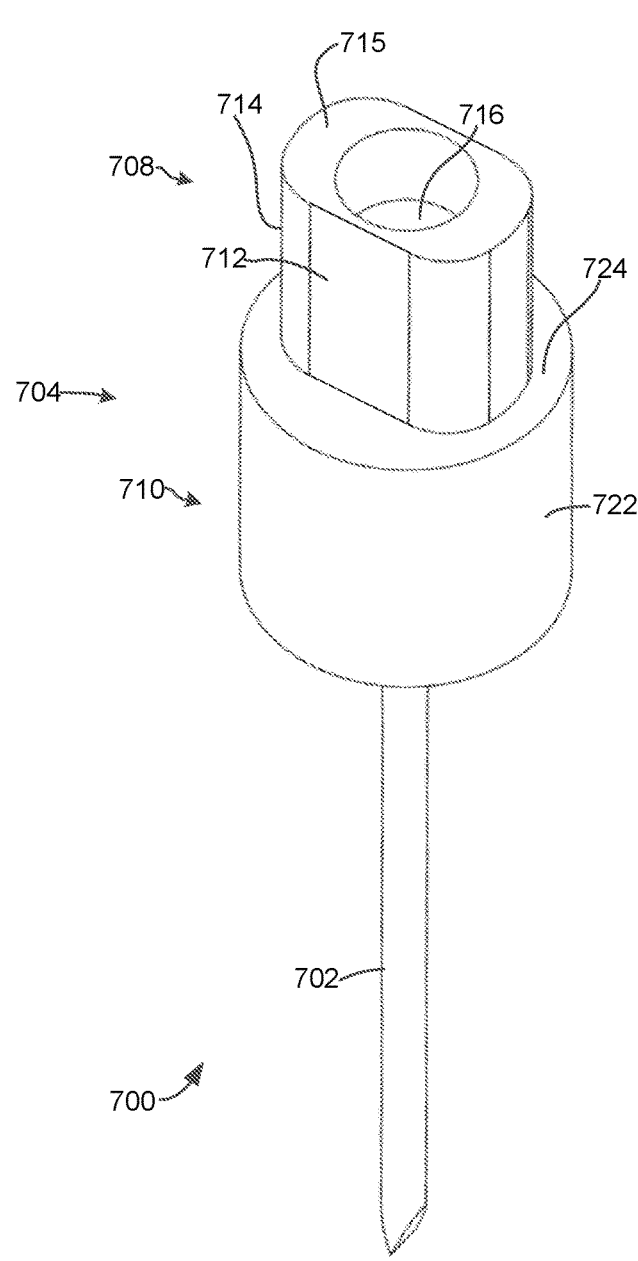
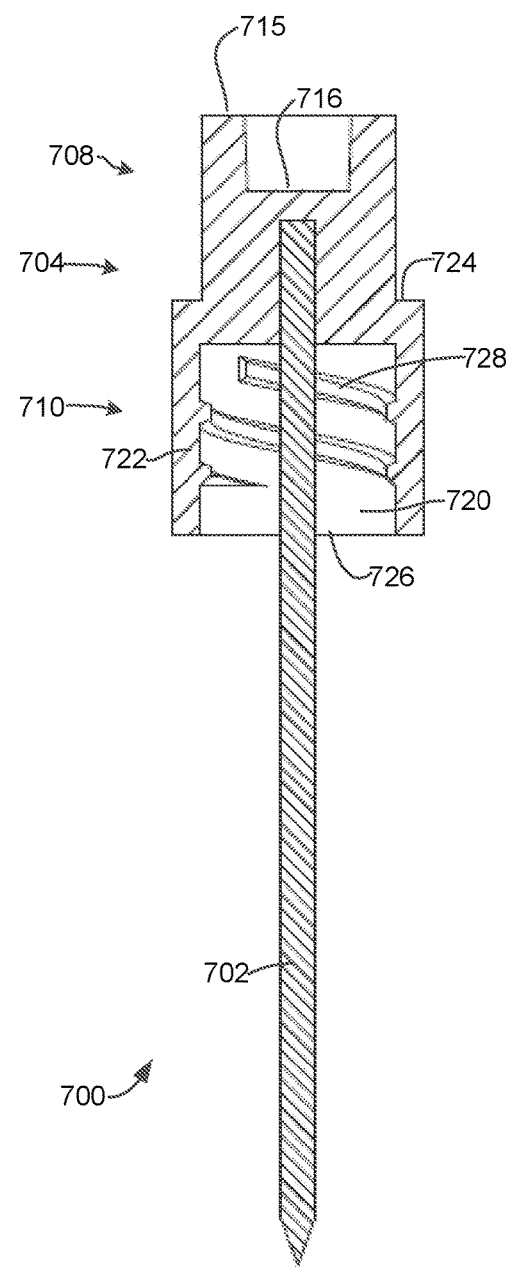
FIG. 8
FIG. 9

INTRAOSSEOUS NEEDLE ASSEMBLY AND METHOD OF USE THEREOF

CROSS-REFERENCE TO RELATED PATENT APPLICATIONS

This application is a Continuation of U.S. patent application Ser. No. 15/844,246, filed on Dec. 15, 2017, the entire disclosure of which is hereby incorporated by reference herein.

BACKGROUND

The present invention relates generally to the field of devices and methods for delivering substances to bone. More particularly, the present invention concerns devices and methods for performing an intraosseous infusion.

An intraosseous infusion is a procedure in which fluid, such as a medication or anesthetic, is delivered to the interior of a bone. When intravenous infusions are difficult or impossible due to tissue damage or small venous size, intraosseous infusions may be preferred because the interior of a bone provides a relatively large and reliable entry point into the venous system protected by a rigid bone cortex. Intraosseous infusions are therefore often used for battlefield or civilian trauma patients and in children who require prompt delivery of fluids such as medications or anesthetics.

An intraosseous infusion is performed by inserting an intraosseous needle into a patient's bone, more particularly through the bone's rigid cortex to a spongy interior section where fluid can be delivered. Some intraosseous needles are designed to be forced into the bone by a blunt impaction force, for example by hitting one end of the needle with a hammer. Other intraosseous needles are designed to be driven into a bone using a specialized power drill. Conventionally, an intraosseous needle is configured to be inserted by only one (i.e., not both) of those two methods.

Once the intraosseous needle is inserted into the patient's bone, fluid is delivered to the interior of the bone through the needle. Conventionally, an intraosseous needle has an open tip through which the fluid is delivered. This tip may become obstructed with bone during or after the insertion process, preventing proper fluid delivery. Another common problem is needle back out, as intraosseous needles typically have a smooth-sided needle shaft prone to sliding back out of the bone along the insertion path. A related complication in intraosseous infusions is the escape of injected fluids from the interior area of the bone targeted by the infusion, known as extravasation. Extravasation can lead to compartment syndrome and severe muscle damage.

BRIEF DESCRIPTION OF THE DRAWINGS

FIG. 8 is a perspective view of a stylet, according to another exemplary embodiment.

FIG. 9 is a cross-sectional side view of the stylet of FIG. 8, according to another exemplary embodiment.

DETAILED DESCRIPTION

Before turning to the figures, which illustrate the exemplary embodiments in detail, it should be understood that the application is not limited to the details or methodology set forth in the description or illustrated in the figures. It should also be understood that the terminology is for the purpose of description only and should not be regarded as limiting.

Figure 1:
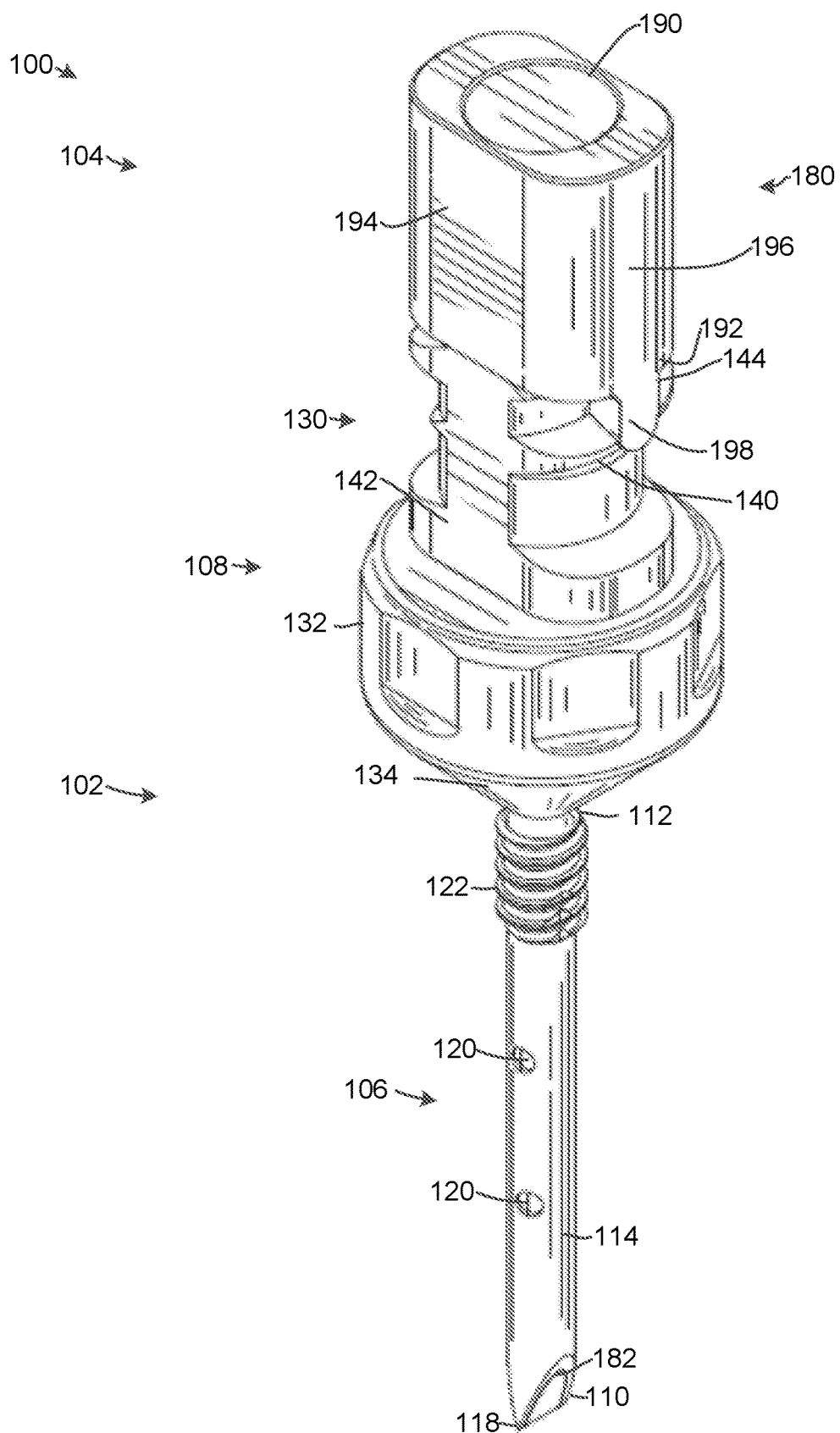
FIG. 1 is a perspective view of an intraosseous needle assembly having a needle and a stylet, according to an exemplary embodiment.

FIG. 1 shows a perspective view of an intraosseous needle assembly 100 according to an exemplary embodiment. Intraosseous needle assembly 100 includes a needle 102 that removably receives a stylet 104. The needle 102 is made up of shaft 106 and needle head 108. The shaft 106 has a distal end 110 and a proximal end 112, and may be substantially cylindrical and smooth-sided. The shaft 106 is hollow, such that the wall 114 of the shaft 106 defines an inner channel 116 (see FIGS. 2A and 3) that runs a length of the shaft from the distal end 110 to the proximal end 112. A tip 118 is at the distal end 110. In the embodiment shown, one or more fenestrations 120 are positioned along the shaft 106, and provide a passage through the wall 114 into the inner channel 116. In other embodiments, the shaft 106 does not include any fenestrations. One or more threads 122 protrude from the wall 114 of the shaft 106 along a proximal portion of the shaft 106, such that the threads 122 are positioned adjacent to the proximal end 112 of the shaft 106.

The needle head 108 extends from the proximal end 112 of the shaft 106. The needle head 108 includes a fitting 130, a geometric torque structure having at least two opposing flat surfaces, such as hexagonal structure 132, and a cone 134. The hexagonal structure 132 is positioned between the fitting 130 and the shaft 106, and the cone 134 is positioned between the hexagonal structure 132 and the shaft 106. A head channel 135 (shown in FIG. 3) aligned with the inner channel 116 of the shaft 106 extends through the needle head 108. As described in detail below with reference to FIG. 2A-3 and 5-6, the fitting 130 includes a latching mechanism 140, a pair of substantially parallel side walls 142, a slot 144, and a receptacle 145 (shown in FIGS. 3 and 5).

As described in detail below, the needle 102 is configured to receive stylet 104. Stylet 104 includes stylet head 180 and stylet shaft 182, shown more clearly in FIGS. 4-5. As configured in FIG. 1, the stylet shaft 182 is placed within the head channel 135 and the inner channel 116, and the stylet head 180 interfaces with the needle head 108. The stylet head 180 has a proximal surface 190 and a distal surface 192, a pair of substantially parallel second side walls 194, a pair of rounded end sections 196 joining the second side walls 194, and a protrusion 198 extending from the distal surface 192 and configured to be received by the slot 144 of the fitting 130. The stylet 104 may be freely removed from the needle 102 and inserted into the needle 102 as needed.

Figure 2A:
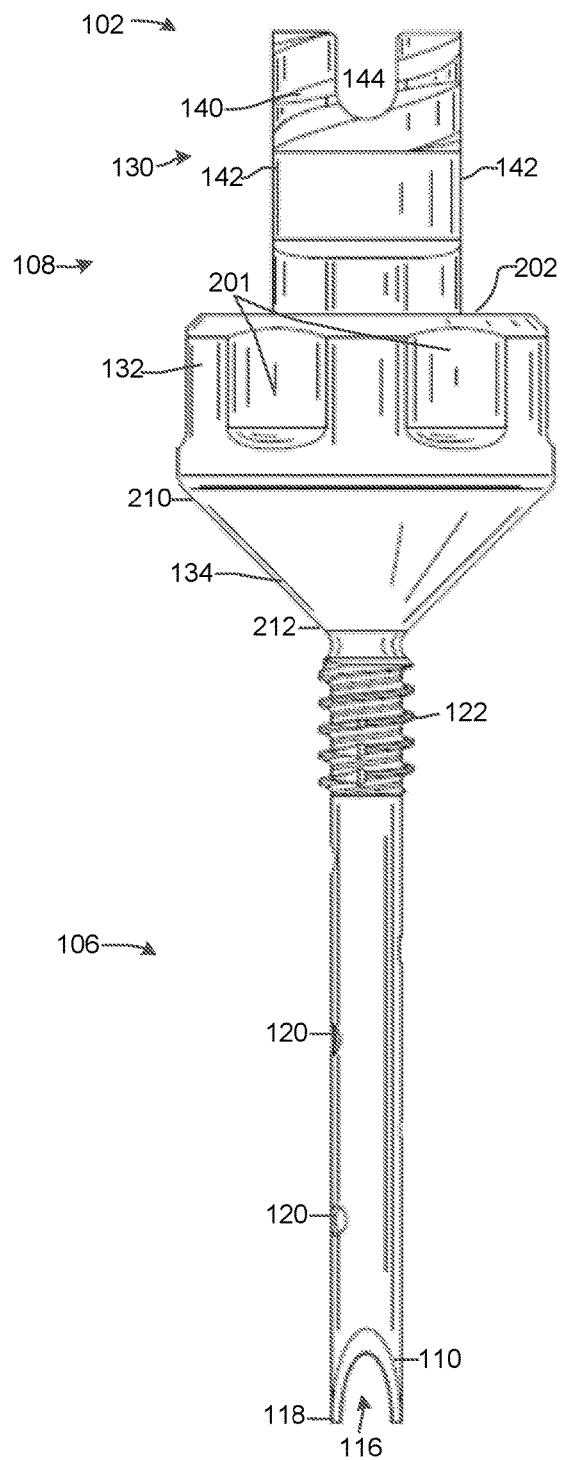
FIG. 2A is a side view of the needle of FIG. 1, according to an exemplary embodiment.
Figure 2B:
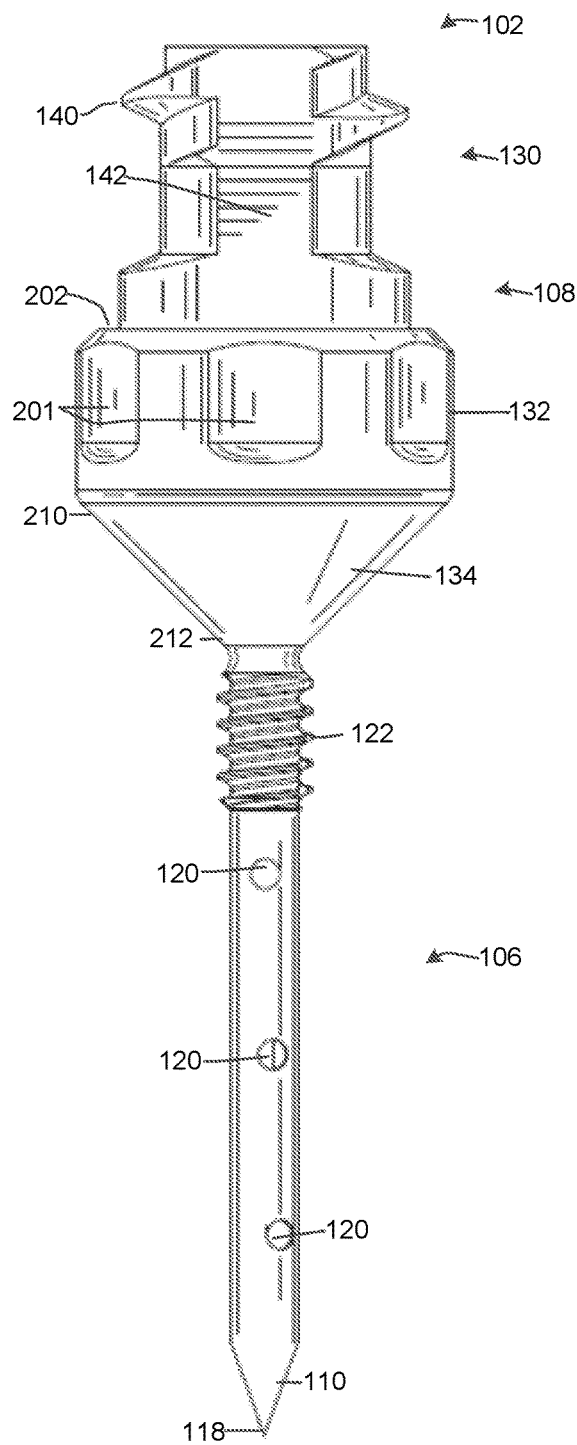
FIG. 2B is another side view of the needle of FIG. 1, according to an exemplary embodiment.
Figure 3:
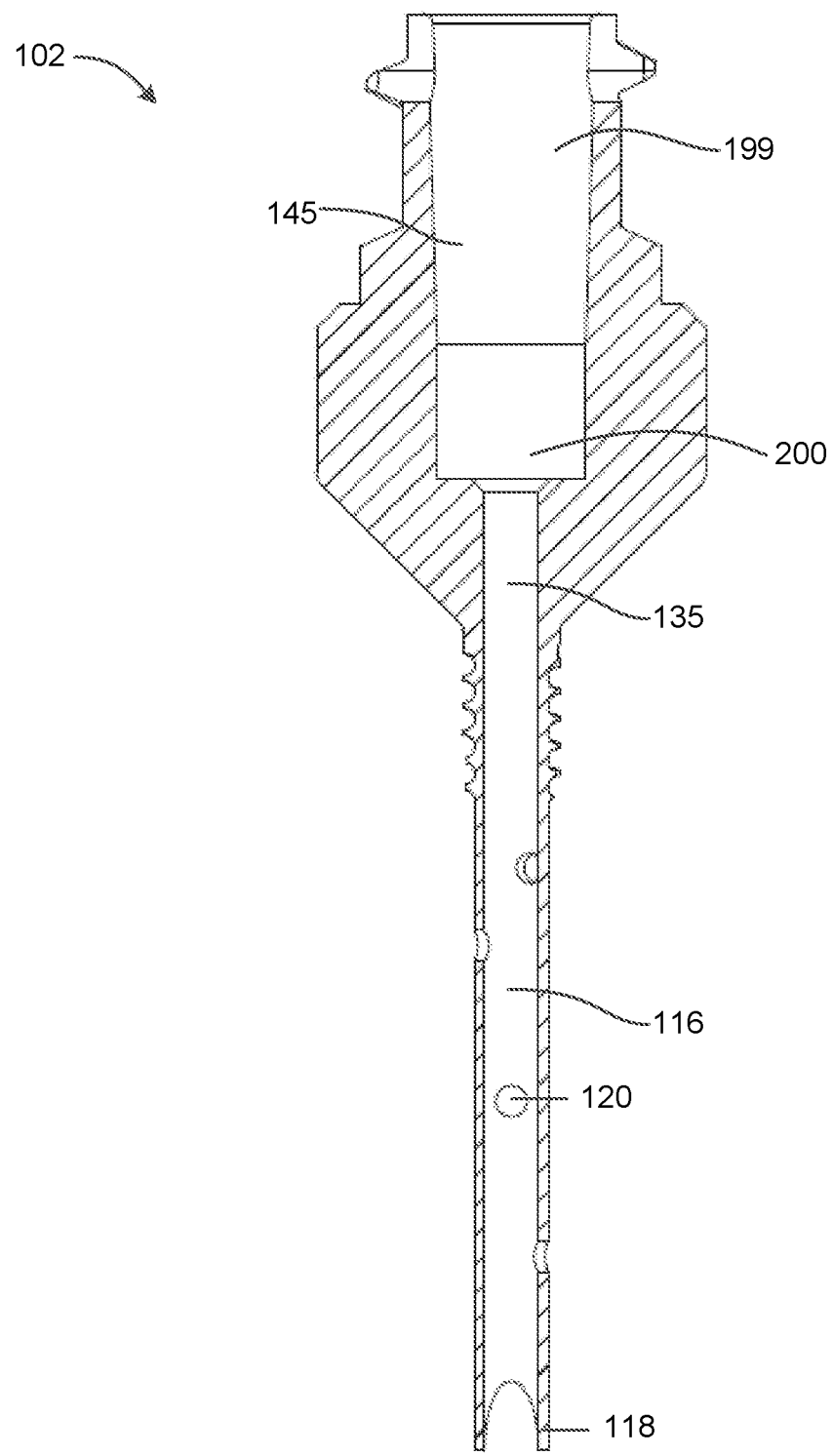
FIG. 3 is a cross-sectional side view of the needle of FIG. 1, according to an exemplary embodiment.

Referring now to FIGS. 2A-B and 3, two side views and a cross-sectional side view of the needle 102 of FIG. 1 are shown, according to an exemplary embodiment. FIG. 3 shows a cross-sectional view of the needle 102 from the same perspective as FIG. 2B. As mentioned above, needle head 108 of the needle 102 has a fitting 130 with a latching mechanism 140 and a receptacle 145. The receptacle 145 and the latching mechanism 140 may be configured to allow the fitting 130 to engage with a standard fluid fitting such as a Luer fitting, or to fit with a specialized fluid input system. For example, the latching mechanism 140 may include threading that can be engaged with corresponding threading on a standard fluid fitting. Infusion fluid may then be supplied to the needle 102 via the fitting 130. More particularly, the fitting 130 may be configured to direct fluid from an outside supply into the head channel 135, which is in fluid communication with the inner channel 116 of the shaft 106. In the embodiment shown in FIG. 3, the receptacle 145 includes a tapered portion 199 and a cylindrical portion 200, configured to receive the stylet 104. In other embodiments, the receptacle 145 may only have the tapered portion 199.

Fitting 130 also includes slot 144, as shown in FIG. 2A. The slot 144 may be configured to receive a standard flat-head screw driver, and may also receive a protrusion 198 of the stylet 104. The slot 144 may be further configured to allow the needle to be twisted by inserting a flat-head screw driver or the stylet 104 into the slot 144 and turning the screw driver or the stylet 104. Fitting 130 also includes substantially parallel side walls 142. Side walls 142 extend from the hexagonal structure 132, and are substantially parallel to the shaft 106. Side walls 142 may be configured to engage a drill chuck on a commercially-available surgical drill used for multiple surgical tasks. Side walls 142 may also be configured to engage with a standard power drill chuck, such as on a general-purpose drill marketed for use in carpentry or other non-medical applications, which may be particularly advantageous in a battlefield setting or for other trauma response outside a medical facility. In some embodiments, the intraosseous needle assembly can only be used with a surgical or general power drill when the needle 102 receives the stylet 104, but in other embodiments the needle 102 may engage with a drill without the stylet 104. The fitting 130 thereby provides multiple modalities of driving the needle 102 into or out of a patient's bone during an intraosseous infusion procedure.

The geometric torque structure, such as hexagonal structure 132, is configured to provide a grip for applying a torque to the needle 102. Torque may be advantageously applied to help tighten or untighten a standard fluid fitting to the latching mechanism 140, or to help remove the needle 102 from a patient's anatomy. The geometric torque structure may include flat panels 201 spaced evenly around a circumference of the geometric torque structure. As shown, the geometric torque structure, such as hexagonal structure 132 includes six flat panels 201, but in alternative embodiments any number of flat panels 201, at least two flat opposing surfaces, may be included in the geometric torque structure. The geometric torque structure also has a flat top platform 202.

Cone 134 is positioned adjacent to the geometric torque structure and has a first end 210 and a second end 212, the first end having a larger diameter than the second end. Cone 134 is substantially cone-shaped and tapers from the first end 210 to the second end 212. The second end 212 may be shaped substantially the same as a cross section of the shaft 106, and is positioned proximate the proximal end of the shaft 106. The shaft 106 may be coupled to the second end 212 of cone 134 such that the inner channel 116 of the shaft 106 is aligned with a head channel 135 that passes through at least part of the needle head 108, to place the inner channel 116 in fluid communication with the head channel 135. In other embodiments, the shaft 106 passes through the cone 134 and the hexagonal structure 132 to define the head channel 135. As shown in FIG. 3, the inner channel 116 and the head channel 135 form a continuous tube fluidly connecting the tip 118 to the receptacle 145. The cone 134 may be configured to push aside anatomical features proximate to the target bone with minimal disruption when the needle 102 is deployed in an intraosseous infusion procedure.

In an infusion procedure, the needle head 108 allows fluid to be introduced into the inner channel 116 of the shaft 106. As mentioned above, inner channel 116 runs from the proximal end 112 of the shaft 106 to the distal end 110. The distal end 110 may be defined by tip 118. Tip 118 may include dual-points with symmetric points on opposing sides of the channel 116 as shown in FIGS. 2A-B. The dual points may be formed by cutting into the wall 114 such that the distal most portions of the tip 118 form dual points. In other embodiments, the tip 118 may be a single-point tip or other needle tip configuration. Tip 118 provides a fluid outlet which allows fluid to flow out of inner channel 116 when fluid is introduced into the inner channel 116.

Fluid may also flow out of the inner channel 116 via fenestrations 120. One or more fenestrations 120 may be distributed on the shaft 106 in any arrangement. Fenestrations 120 may be substantially circular or may be some other shape. Fenestrations 120 can thereby provide a way for fluid to be infused at a variety of locations within a target bone by providing channels for output flows of fluid at different locations along the shaft 106. Fenestrations 120 also provide an alternative fluid outlet when bone or other material clogs an opening in the tip 118. In some embodiments, tip 118 may be a closed point, such that fluid only flows out of the inner channel 116 via fenestrations 120.

One or more threads 122 are positioned along a portion of the shaft 106 near or adjacent to the proximal end 112 of the shaft 106. The rest of the shaft 106 may be smooth, allowing the shaft to be driven through a bone by an impaction force when desired. When the needle 102 is deployed in a bone for an intraosseous infusion procedure, the needle 102 may be twisted to engage the one or more threads 122 with the bone's hard cortex. The one or more threads 122 may then secure the needle 102 to the bone to prevent or reduce the risk of needle movement, such as needle back out. The one or more threads 122 may also help to prevent fluid infused into the bone through the needle 102 from escaping from the interior of the bone along the boundary between the needle 102 and the bone's cortex. The one or more threads 122 may therefore reduce the risk of extravasation.

Figure 4:
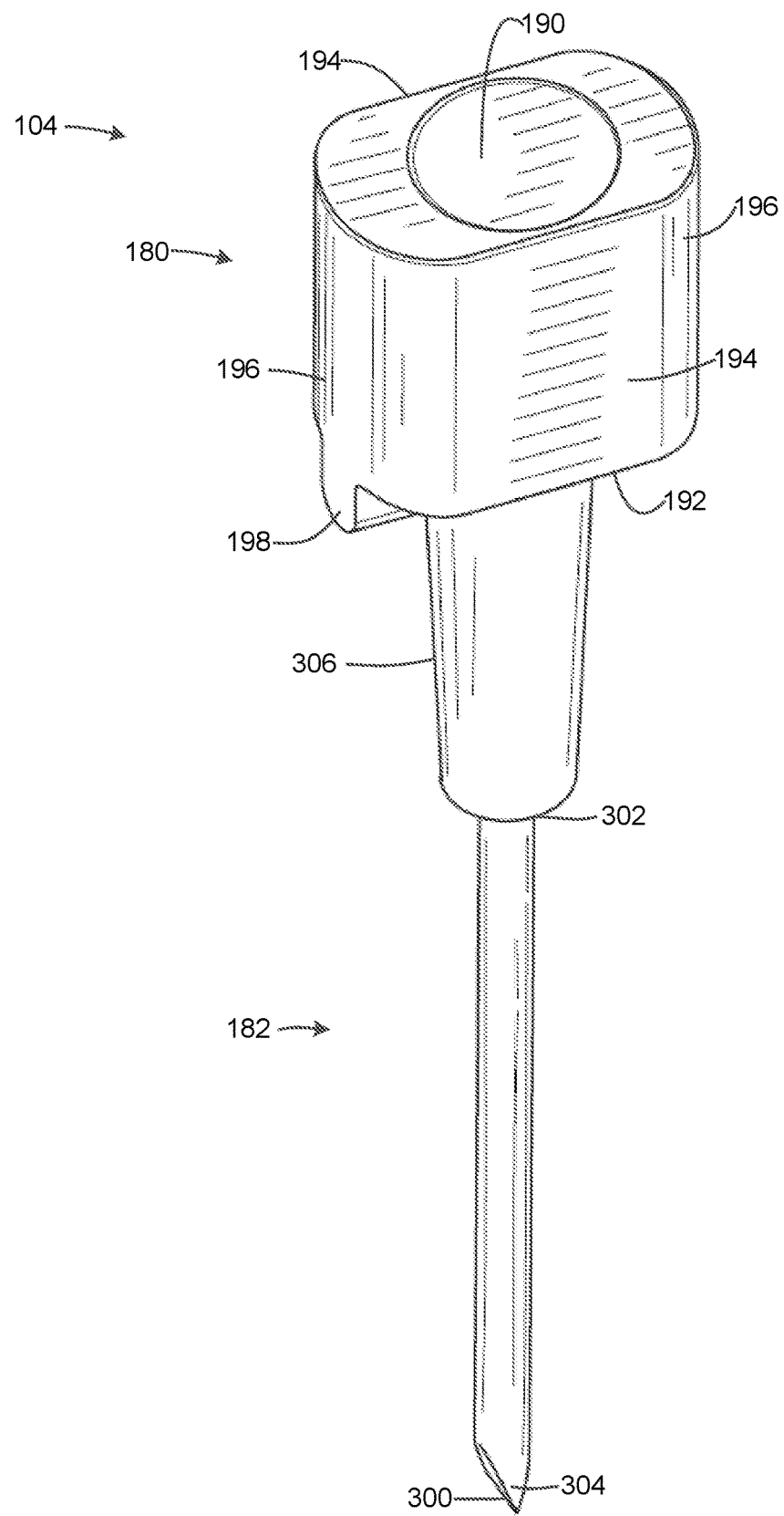
FIG. 4 is a perspective view of the stylet of FIG. 1, according to an exemplary embodiment.
Figure 6:
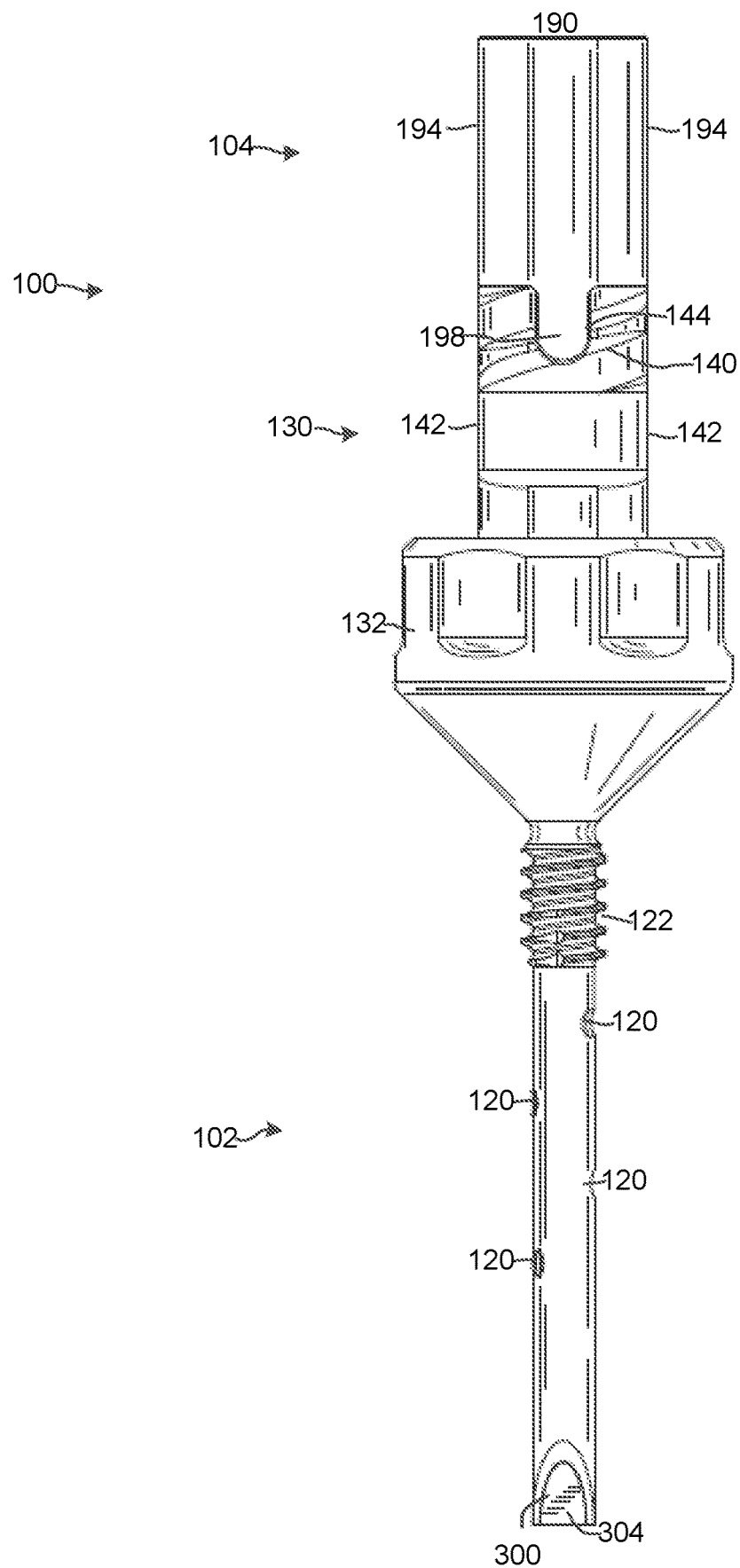
FIG. 6 is a side view intraosseous needle assembly of FIGS. 1 and 5, according to an exemplary embodiment.

Referring now to FIG. 4, a perspective view of the stylet 104 of FIG. 1 is shown, according to an exemplary embodiment. The stylet 104 includes stylet head 180 and stylet shaft 182. The stylet shaft 182 has a first end 300 and a second end 302, with a tip 304 at the first end. The stylet shaft 182 is shaped and sized substantially the same as a combination of the inner channel 116 of the needle shaft 106 and the head channel 135 of the needle head 108, so that the stylet shaft substantially fills the inner channel 116 and the head channel 135 when the needle 102 receives the stylet 104. The stylet tip 304 may be formed by two walls angled towards one another and ending in a pointed edge. The stylet tip is configured to fill an opening in the needle tip 118. As shown in FIG. 6, the pointed edge is configured to be aligned with the dual points of the needle tip 118 and the angled walls aligned with the areas cut into the needle shaft wall 114.

Stylet head 180 has a proximal surface 190 and distal surface 192. Proximal surface 190 may be substantially flat and may provide a surface to be struck with a mallet, hammer, or other object capable of delivering an impaction force. A pair of substantially parallel side walls 194 run from the proximal surface 190 to the distal surface 192, and are joined by rounded end sections 196.

Proximal surface 190, distal surface 192, side walls 194, and/or rounded end sections 196 may be configured to engage a drill chuck on a commercially-available surgical drill used for multiple surgical tasks, and may also be configured to engage with a standard power drill chuck, such as on a general-purpose drill marketed for use in carpentry or other non-surgical application. The space bounded by the proximal surface 190, the distal surface 192, the side walls 194, and the rounded end sections 196 may be filled with a solid material or may be hollow. A protrusion 198 protrudes from distal surface 192, and may be shaped substantially like the tip of a standard flat-head screw driver or may have a semi-circular shape. Protrusion 198 is configured to be received by the slot 144 of the needle head 108. A tapered section 306 also extends from the distal surface towards the stylet shaft 182. The tapered section 306 is coupled to the stylet shaft 182. The tapered section 306 is shaped to be received by the receptacle 145 of the fitting 130.

Figure 5:
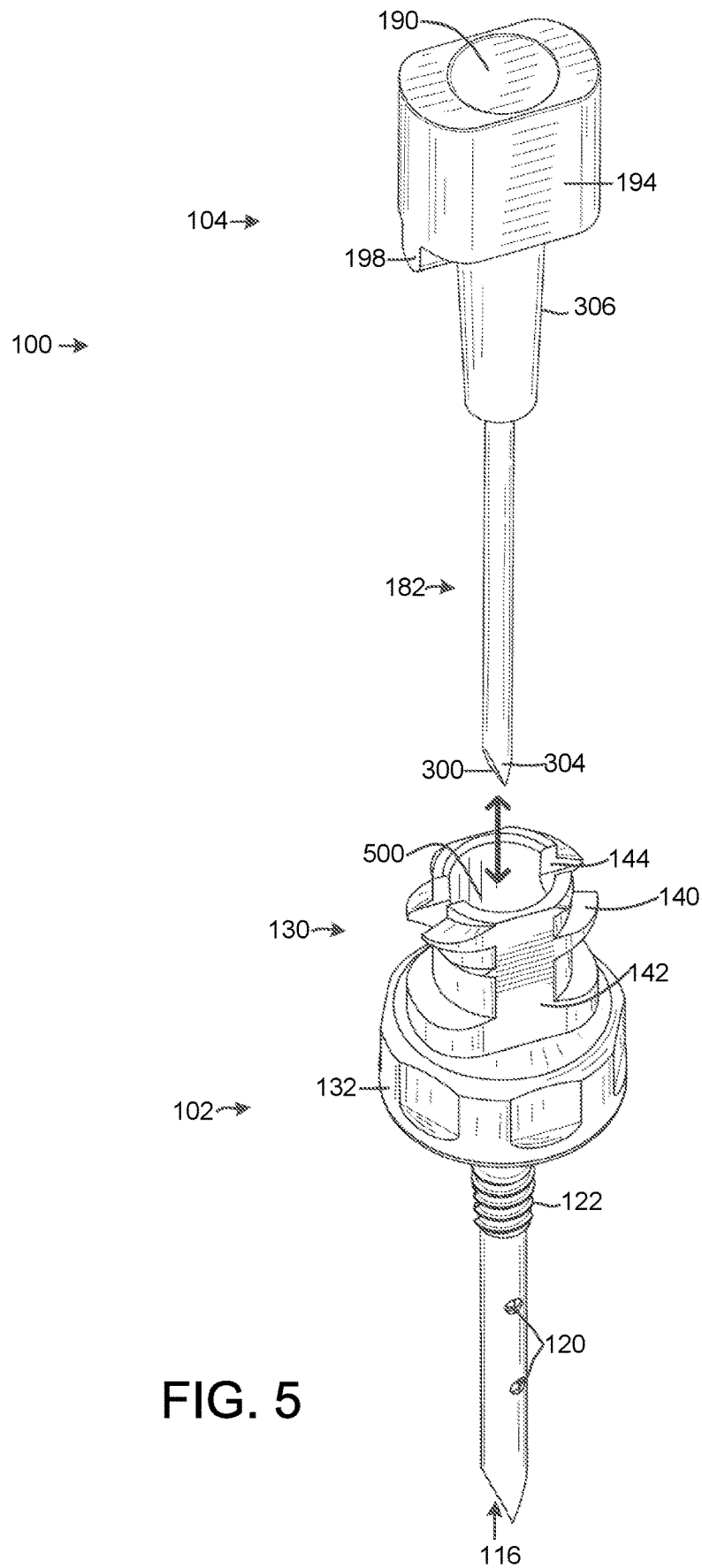
FIG. 5 is perspective view of the intraosseous needle assembly of FIG. 1, according to an exemplary embodiment.

Referring now to FIG. 5, the intraosseous needle assembly 100 of FIG. 1 is shown with the stylet 104 removed from the needle 102, according to an exemplary embodiment. FIG. 5 illustrates that the stylet 104 and the needle 102 are separate pieces configured to be used together in an intraosseous infusion procedure The stylet 104 may be inserted into the needle 102 by directing the first end 300 of the stylet shaft 182 into the receptacle 145 of the fitting 130 and sliding the stylet shaft 182 into the inner channel 116 of the needle shaft 106, and may be removed along the same path. The tapered section 306 may be inserted into the receptacle 145. The protrusion 198 can be aligned with and inserted into the slot 144. In some embodiments, a snapping mechanism is included that secures the stylet to the needle.

Referring now to FIG. 6, which illustrates a side view of the intraosseous needle assembly 100 with stylet 104 received by the needle 102, according to an exemplary embodiment, when the needle 102 receives the stylet 104, the stylet shaft 182 substantially fills the inner channel 116 of the needle shaft 106. In this configuration, the stylet shaft 182 can prevent bone or other tissue from entering the inner channel 116 when the needle assembly 100 is inserted into a patient's bone. The stylet shaft 182 may absorb much of the force, strain, or stress that would otherwise be placed on the needle shaft 106, and thereby helps to protect the needle shaft 106 from deformation. The tip 304 may be sharpened to help the intraosseous needle assembly 100 penetrate a patient's anatomy.

In the configuration shown in FIG. 6, the tapered section 306 is received entirely inside the receptacle 145. Protrusion 198 fits snuggly within slot 144, which forces a rotation of the stylet head 180 to cause the needle 102 to rotate as well. When the protrusion 198 is received by the slot 144, the side walls 142 of the fitting 130 and the side walls 194 of the stylet head 180 are substantially co-planar. The combination of the stylet head 180 and the fitting 130 thereby form a structure that can engage a chuck on a surgical drill or a general purpose drill. The alignment also allows an impaction force applied to the proximal surface 190 of the stylet head 180 to be transferred to the rest of the intraosseous needle assembly 100.

To carry out an intraosseous infusion procedure using intraosseous needle assembly 100, the stylet 104 is inserted into the needle 102, with the protrusion 198 received by the slot 144 as in FIG. 6. The intraosseous infusion needle assembly 100 may then be optionally be driven into a bone using a drill or forced into the bone using an impaction force. Once the needle shaft 106 is within the bone, the needle 102 may be twisted to engage the threading 122 with the cortex of the bone. The needle 102 may be twisted using a drill, by hand by gripping the stylet head 180, the fitting 130, and/or the geometric torque structure, such as hexagonal structure 132, or by removing the stylet 104 and engaging a flat-head screw driver with slot 144. Once tightened, the needle 102 is self-retained to the patient's anatomy.

The stylet 104 may then be removed from the needle 102. The stylet 104 may be disposable, or may be configured for re-sterilization for future reuse. When the stylet 104 is removed, the receptacle 145, the head channel 135, and the inner channel 116 are left as open space, all in fluid communication. A standard fluid coupling may be latched to fitting 130 by latching mechanism 140, in order to place an external fluid source in fluid communication with the head channel 135 and the inner channel 116. Geometric torque structure, such as hexagonal structure 132 may provide a grip to provide counter-torque when tightening or untightening a fluid coupling onto fitting 130.

Fluid may then flow through the inner channel 116 and into the patient's bone through tip 118 and fenestrations 120. A plurality of outputs provided by tip 118 and fenestrations 120 ensures that another output flow continues if the tip 118 or one of the one or more fenestrations 120 becomes blocked or clogged. Fluid such as medication or anesthetic may thereby be provided to a patient.

After the desired fluid is infused into the bone, the needle 102 may be removed from the bone. The needle 102 must be twisted (in an opposite direction) to disengage the one or more threads 122 from the bone. This twisting may be achieved by gripping and turning the needle head 108, by inserting a flat-head screw driver into the slot 144 and twisting the screw driver, by reinserting the stylet 104 and twisting the stylet, or by engaging the intraosseous needle assembly with a drill and operating the drill to disengage the threading 122 from the bone. Once the threading 122 is disengaged from the bone, the needle 102 may be pulled out of the patient.

Figure 7:
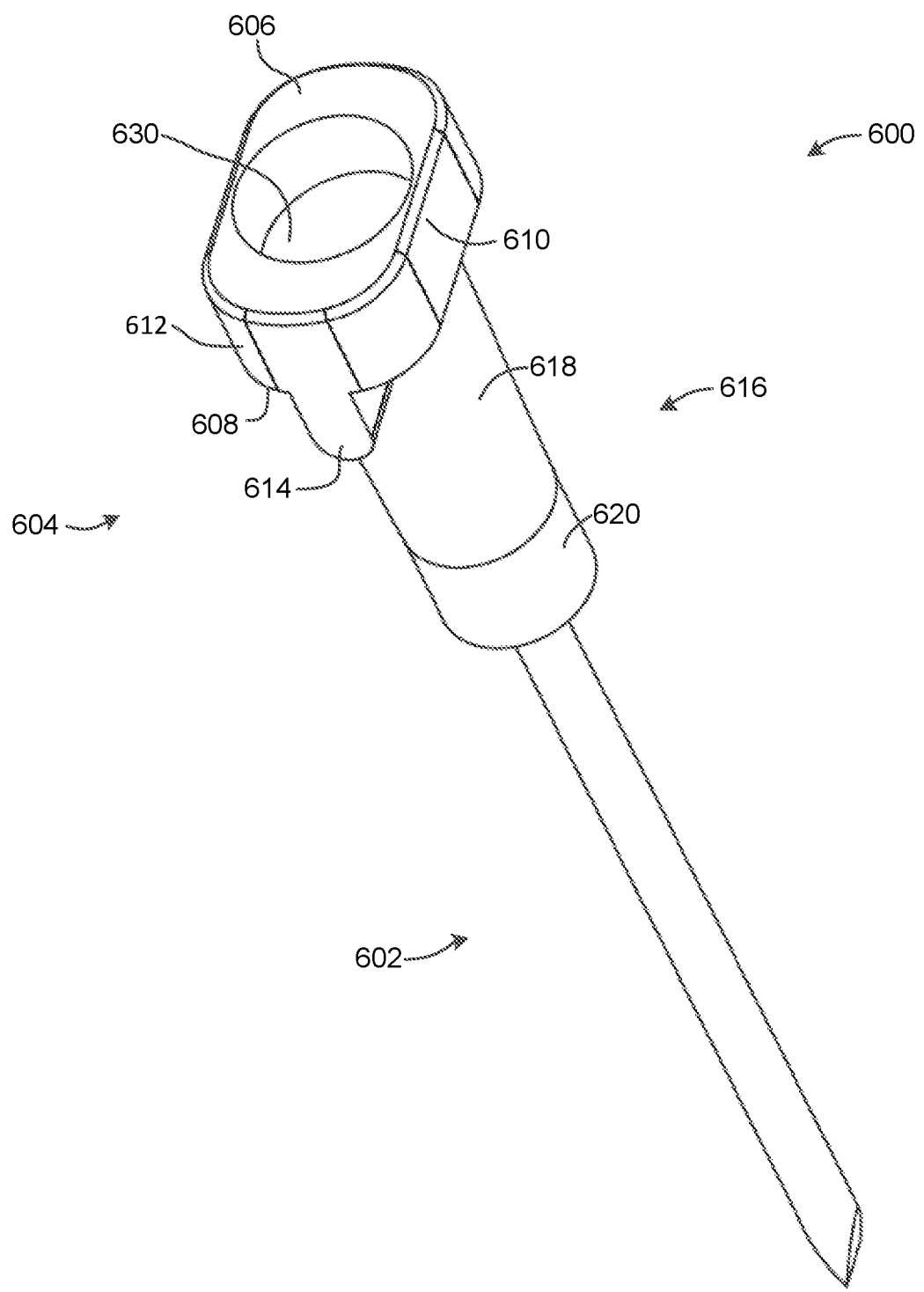
FIG. 7 is a perspective view of a stylet, according to another exemplary embodiment.

Referring now to FIG. 7, another stylet for use with the needle 102 is shown, according to an exemplary embodiment. Stylet 600 has a shaft 602 and a stylet head 604. The stylet head 604 is defined by a top surface 606 and a bottom surface 608. A pair of substantially parallel side walls 610 and a pair of curved end sections 612 extend from the top surface 606 to the bottom surface 608. A protrusion 614 protrudes from the bottom surface 608 and is configured to engage the slot 144 on the fitting 130. Stylet head 604 also includes a projection 616 configured to be received by the receptacle 145. In the embodiment shown in FIG. 6, projection 616 includes both a tapered section 618 and a cylindrical section 620. When the projection 616 is received by the receptacle 145, the tapered section 618 substantially fills the tapered portion 199 of the receptacle 145 (shown in FIG. 3), and the cylindrical section 620 substantially fills the cylindrical portion 200 (shown in FIG. 3). The projection 616 is configured to efficiently transfer an impaction force (e.g., a blow, strike, etc. from a hand, mallet, hammer, etc.)

applied to the top surface 606 to the shaft 602 and the needle 102 internally through the needle head 108.

The stylet 600 also includes a circular depression 630 depressed into the top surface 606. Circular depression 630 is substantially aligned with the projection 616. Circular depression 630 is configured to receive a tool, device, or object for facilitating the delivery of an impaction force to the stylet 600. Circular depression 630 may thereby ensure that the impaction force is delivered in line with the projection 616 and the shaft 602 to optimize the effectiveness of the impaction force in driving the needle assembly 100 into a bone. Circular depression 630 may also be configured to help engage the stylet with a drill.

Referring now to FIGS. 8 and 9, another stylet for use with the needle 102 is shown, according to an exemplary embodiment. Stylet 700 has a shaft 702 and a stylet head 704. The stylet head 704 includes an end portion 708 and cylindrical portion 710. The end portion 708 includes a pair of substantially parallel side walls 712, rounded end sections 714, a top surface 715, and a circular depression 716, which may generally be configured like the corresponding elements of the stylet 104 shown in FIG. 4 and/or the stylet 600 shown in FIG. 7. The shaft 702 is coupled to the end portion 708 and extends partially through the end section 708. The remainder of the shaft 702 extends out of a bottom end 718 of the end portion 708.

The cylindrical portion 710 includes an interior space 720 defined by a cylinder wall 722 and a closed top 724, within an opening 726 opposite the closed top 724. The closed top 724 abuts the bottom end 718 of the end portion 708. The shaft 702 extends from the end portion 708, through the closed top 724 and the interior space 720, and out the opening 726. The cylinder wall 722 is centered on the shaft 702 defines the central axis of the cylinder wall 722. Cylinder wall 722 includes threading 728 that extends into the interior space 720.

Figure 10:
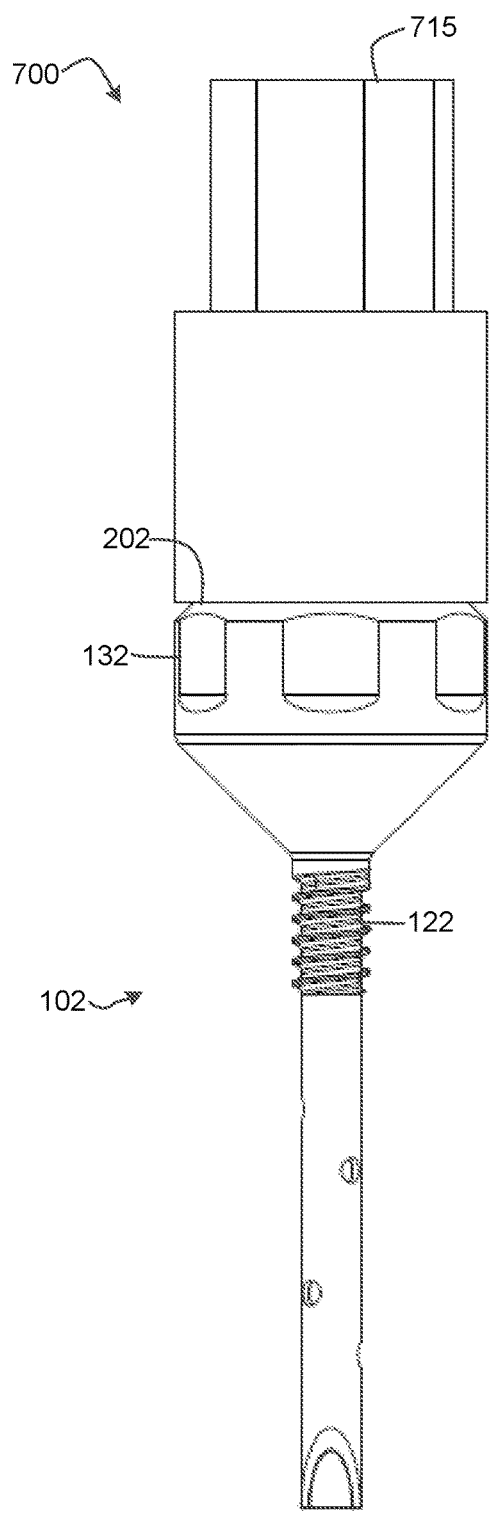
FIG. 10 is a side view of an intraosseous needle assembly having a needle and the stylet of FIG. 8, according to an exemplary embodiment.
Figure 11:
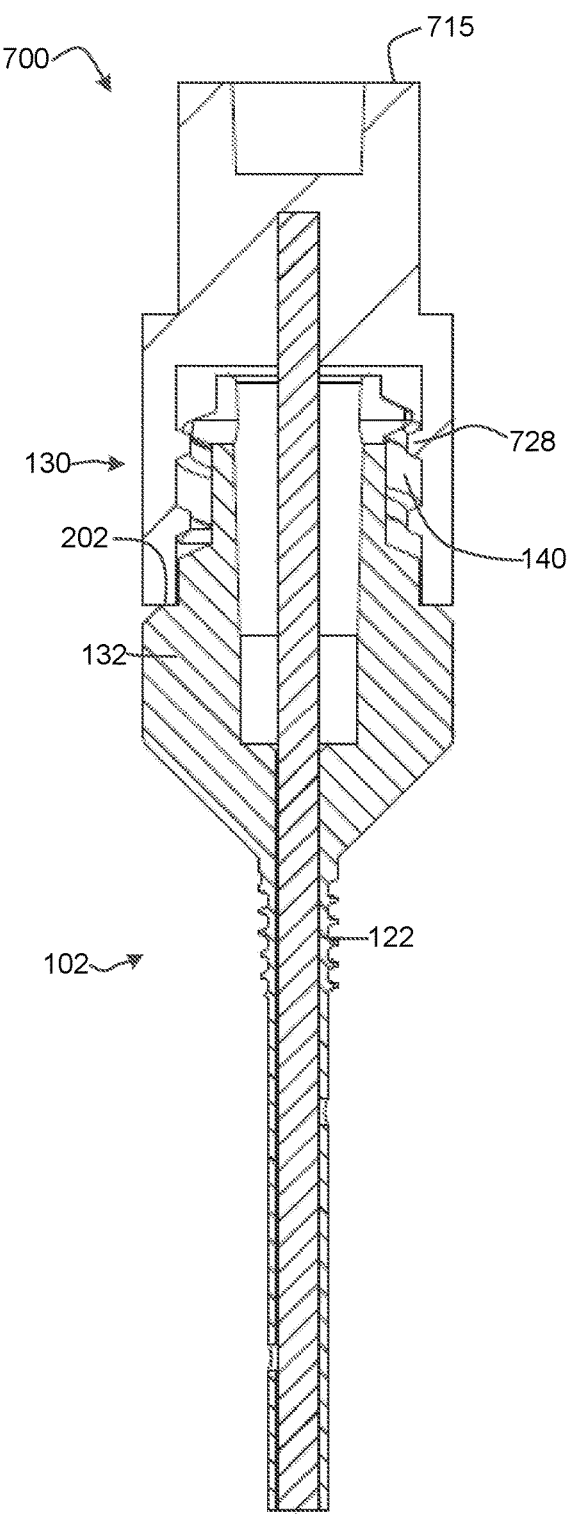
FIG. 11 is a cross-sectional side view of the intraosseous needle assembly of FIG. 10, according to an exemplary embodiment.

Referring now to FIGS. 10 and 11, a side-view and a cross-sectional view of an intraosseous needle assembly with the stylet 700 of FIGS. 8-9 is shown, according to an exemplary embodiment. As shown, the interior space 720 of the stylet 700 is configured to receive the fitting 130 of the needle 102. The threading 728 engages the latching mechanism 140 to removably secure the stylet 700 to the needle 102. Threading 728 may have a configuration that matches the design of standard fluid couplings, which the latching mechanisms 140 are configured to engage. In some embodiments, the threading 122 on the needle 102 is oriented such that the direction of rotation of the stylet that tightens the threading 728 on the latching mechanism 140 (e.g., clockwise) is also the direction of rotation that engages the threading 122 with a bone. When the threading 278 fully engages the latching mechanism 140, continued twisting of the stylet in the tightening direction can therefore cause the threading 122 to engage a bone. The stylet 700 can thus be used with a drill to drive the needle 102 into a bone.

When the threading 728 fully engages the latching mechanism 140, the cylinder wall 722 abuts the top platform 202 of the hexagonal structure 132. An impaction force applied to the top surface 715 can be transferred to the hexagonal structure 132 by the cylinder wall 722. The impaction force thus passes around the fitting 130, limiting the risk of damage to the receptacle 145 or the head channel 135. The stylet 700 thus allows the needle 102 to be driven into a bone by an impaction force.

The intraosseous needle assembly described herein thereby provides a system for intraosseous infusions that may be inserted into a patient's bone using any of an impaction force, a surgical drill, or a general-purpose drill that engages a bone cortex to self-retain within the bone, and that allows infusion fluid to flow into a patient's bone through multiple outlets.

The construction and arrangement of the devices and methods as shown in the various exemplary embodiments are illustrative only. Although only a few embodiments have been described in detail in this disclosure, many modifications are possible (e.g., variations in sizes, dimensions, structures, shapes and proportions of the various elements, use of materials, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

What is claimed is:

1. An intraosseous needle comprising:
   a cylindrical shaft comprising:
      a first portion comprising a plurality of threads protruding from the cylindrical shaft; and
      a second portion comprising a plurality of fenestrations, disposed between the first portion and a distal end of the cylindrical shaft, wherein the cylindrical shaft is continuous and smooth within the second portion; and
   a needle head extending from a proximal end of the cylindrical shaft, wherein the needle head comprises a geometric torque structure, the geometric torque structure comprising at least two opposing flat surfaces, and wherein a pair of substantially parallel first side walls extend from the geometric torque structure.

2. The intraosseous needle of claim 1, wherein the plurality of fenestrations are formed in a wall of the cylindrical shaft extending to an inner channel.

3. The intraosseous needle of claim 1, wherein the plurality of threads are configured to engage a bony cortex when the needle is inserted into a bone.

4. The intraosseous needle of claim 1, further comprising an open tip at the distal end.

5. The intraosseous needle of claim 1, wherein the needle head further comprises a fitting comprising a slot and the pair of substantially parallel first side walls.

6. The intraosseous needle of claim 5, wherein the fitting comprises a latching mechanism and a receptacle.

7. The intraosseous needle of claim 1, wherein the needle head further comprises a head channel aligned with an inner channel of the cylindrical shaft and extending through the needle head.

8. The intraosseous needle of claim 7, further comprising a stylet.

9. The intraosseous needle of claim 8, wherein the stylet comprises:
   a second cylindrical shaft having a first end and a second end; and
   a stylet head extending from the second end, the stylet head comprising:
      a proximal surface and a distal surface;
      a pair of substantially parallel second side walls extending from the proximal surface to the distal surface;

a pair of rounded end sections joining the second side walls;

a protrusion extending from the distal surface; and a tapered section extending from the distal surface to the second cylindrical shaft.

10. The intraosseous needle of claim 9, wherein the second cylindrical shaft is shaped substantially the same as a combination of the inner channel and the head channel.

11. The intraosseous needle of claim 9, wherein the needle head further comprises a fitting comprising a slot, a receptacle, and the pair of substantially parallel first side walls; and wherein the protrusion of the stylet head is configured to be received by the slot, and wherein the tapered section is configured to be received by the receptacle.

12. The intraosseous needle of claim 9, wherein the stylet head and a fitting of the needle head are configured to engage with a drill when the cylindrical shaft and the needle head receive the stylet, and wherein the intraosseous needle can be inserted into a bone using the drill.

13. The intraosseous needle of claim 9, wherein the proximal surface of the stylet head is configured to receive an impaction force when the cylindrical shaft and the needle head receive the stylet, and wherein the intraosseous needle can be inserted into a bone by the impaction force.

14. The intraosseous needle of claim 9, wherein the intraosseous needle can be inserted into a bone using a drill wherein the stylet head and a fitting of the needle head are configured to engage with the drill when the cylindrical shaft and the needle head receive the stylet; and wherein the proximal surface of the stylet head is configured to receive an impaction force when the cylindrical shaft and the needle head receive the stylet, and wherein the intraosseous needle can be inserted into the bone by the impaction force.

15. A method of applying a fluid to an interior of a bone, comprising:

inserting an intraosseous needle into the bone, wherein the intraosseous needle comprises:

a cylindrical shaft comprising:

a first portion comprising a plurality of threads protruding from the cylindrical shaft; and a second portion comprising a plurality of fenestrations, disposed between the first portion and a distal end of the cylindrical shaft, wherein the cylindrical shaft is continuous and smooth within the second portion;

a needle head extending from a proximal end of the cylindrical shaft, wherein the needle head comprises a geometric torque structure, the geometric torque structure comprising at least two opposing flat surfaces, and wherein a pair of substantially parallel first side walls extend from the geometric torque structure; and at least one fluid outlet providing a fluid path between an inner channel of the cylindrical shaft and the interior of the bone;

twisting the intraosseous needle around an axis extending along the inner channel to engage the plurality of threads with a cortex of the bone; and providing the fluid to the inner channel to infuse the bone with the fluid via the at least one fluid outlet.

16. The method of claim 15, wherein the intraosseous needle is inserted into the bone using at least one of an impaction force or a drill.

17. The method of claim 15, wherein the needle head comprises a fitting in fluid communication with the inner channel, wherein the method further comprises securing a fluid source to the fitting for providing the fluid to the inner channel.

18. The method of claim 15, wherein the twisting is carried out using at least one of a drill engaged with the intraosseous needle, a screwdriver engaged with the intraosseous needle, a stylet received by the intraosseous needle, or a force applied to the geometric torque structure coupled to the cylindrical shaft.

19. An intraosseous needle comprising:

a cylindrical shaft comprising:

a first portion comprising a plurality of threads protruding from the cylindrical shaft; and a second portion comprising a plurality of fenestrations, disposed between the first portion and a distal end of the cylindrical shaft, wherein the cylindrical shaft is continuous and smooth within the second portion, and wherein the continuous, smooth second portion is longer than the first portion; and a needle head extending from a proximal end of the cylindrical shaft, wherein the needle head further comprises a cone positioned between a geometric torque structure and the cylindrical shaft.

20. The intraosseous needle of claim 19, wherein the plurality of threads are configured to engage a bony cortex when the needle is inserted into a bone.

* * * * *